(12) United States Patent
Mousses et al.

(10) Patent No.: US 8,898,149 B2
(45) Date of Patent: Nov. 25, 2014

(54) BIOLOGICAL DATA STRUCTURE HAVING MULTI-LATERAL, MULTI-SCALAR, AND MULTI-DIMENSIONAL RELATIONSHIPS BETWEEN MOLECULAR FEATURES AND OTHER DATA

(75) Inventors: Spyro Mousses, Scottsdale, AZ (US); Toni R. Farley, Chandler, AZ (US); Jeffrey A. Kiefer, Phoenix, AZ (US); Charles J. Colbourn, Phoenix, AZ (US); Preston Victor Lee, Phoenix, AZ (US)

(73) Assignees: The Translational Genomics Research Institute, Phoenix, AZ (US); Arizona Board of Regents on Behalf of Arizona State University, Tempe, AZ (US)

( * ) Notice: Subject to any disclaimer, the term of this patent is extended or adjusted under 35 U.S.C. 154(b) by 150 days.

(21) Appl. No.: 13/463,603

(22) Filed: May 3, 2012

(65) Prior Publication Data
US 2012/0284257 A1    Nov. 8, 2012

Related U.S. Application Data

(60) Provisional application No. 61/483,248, filed on May 6, 2011, provisional application No. 61/555,217, filed on Nov. 3, 2011, provisional application No. 61/596,859, filed on Feb. 9, 2012.

(51) Int. Cl.
| | | |
|---|---|---|
| *G06F 7/00* | (2006.01) | |
| *G06F 17/30* | (2006.01) | |
| *C12Q 1/68* | (2006.01) | |
| *G06F 19/28* | (2011.01) | |
| *G06F 15/16* | (2006.01) | |

(52) U.S. Cl.
CPC .......... *G06F 19/28* (2013.01); *C12Q 2600/106* (2013.01); *G06F 17/30554* (2013.01); *Y10S 707/941* (2013.01)

USPC .......... 707/722; 707/941; 435/6.13

(58) Field of Classification Search
CPC .......... G06F 17/30554; Y10S 707/941; C12Q 2600/106
USPC .......... 707/722, 941; 435/6.13
See application file for complete search history.

(56) References Cited

U.S. PATENT DOCUMENTS

| | | |
|---|---|---|
| 5,706,498 A | 1/1998 | Fujimiya et al. |
| 5,724,253 A | 3/1998 | Skovira |

(Continued)

OTHER PUBLICATIONS

Farley, Toni, et al., "A Hypergraph Data Model and Query Language for Designing a Biomedical Knowledge Base", Journal of the American Medical Informatics Association, Published: Jan. 2013, vol. 20 Issue: 1 pp. 128-133, published by group.bmj.com.

*Primary Examiner* — Greta Robinson
*Assistant Examiner* — Brian E. Weinrich

(57) ABSTRACT

A computer system maintains a biological data structure having molecular feature data. The system receives data elements indicating biological molecular features and knowledge elements that represent biological concepts. The system individually associates unique identifiers with the elements. For individual elements, the system maintains an internal element set of the other unique identifiers for the other elements that are directly associated with that one individual element. For the individual elements, the system maintains an external element set of the other unique identifiers for the other elements that have that one individual element in their own internal element sets. Although not required, the computer system may process a query indicating a search scope and a molecular feature for an individual biological entity, and responsively process the molecular feature and the elements based on the search scope to induce a knowledge sub-graph for the individual biological entity.

2 Claims, 13 Drawing Sheets

(56) References Cited

U.S. PATENT DOCUMENTS

| | | |
|---|---|---|
| 5,924,074 A | 7/1999 | Evans |
| 5,953,727 A * | 9/1999 | Maslyn et al. ............... 435/6.12 |
| 6,023,659 A | 2/2000 | Seilhamer et al. |
| 6,223,186 B1 | 4/2001 | Rigault et al. |
| 6,303,297 B1 | 10/2001 | Lincoln et al. |
| 6,408,308 B1 | 6/2002 | Maslyn et al. |
| 6,453,333 B1 | 9/2002 | Glynias et al. |
| 6,640,211 B1 | 10/2003 | Holden |
| 6,675,166 B2 | 1/2004 | Bova |
| 6,687,685 B1 | 2/2004 | Sadeghi et al. |
| 6,687,692 B1 * | 2/2004 | Balaban et al. ........ 707/999.006 |
| 6,742,004 B2 | 5/2004 | Sabatini et al. |
| 6,804,679 B2 | 10/2004 | Jevons et al. |
| 6,816,867 B2 | 11/2004 | Jevons et al. |
| 6,922,638 B1 | 7/2005 | Wallace et al. |
| 6,931,396 B1 | 8/2005 | Topaloglou et al. |
| 7,020,561 B1 * | 3/2006 | McLoughlin et al. .......... 702/19 |
| 7,392,199 B2 | 6/2008 | Karlov et al. |
| 7,428,527 B2 | 9/2008 | Watanabe et al. |
| 7,493,265 B2 | 2/2009 | Fagan et al. |
| 7,788,040 B2 * | 8/2010 | Haskell et al. .................. 702/19 |
| 7,853,626 B2 * | 12/2010 | Jung et al. ..................... 707/812 |
| 7,865,534 B2 | 1/2011 | Chandra et al. |
| 7,912,650 B2 | 3/2011 | Kato et al. |
| 2004/0002818 A1 * | 1/2004 | Kulp et al. ...................... 702/20 |
| 2005/0009078 A1 * | 1/2005 | Craford et al. .................. 702/20 |
| 2005/0038608 A1 * | 2/2005 | Chandra et al. ......... 707/999.003 |
| 2006/0020398 A1 * | 1/2006 | Vernon et al. ................... 702/20 |
| 2007/0172844 A1 | 7/2007 | Lancaster et al. |
| 2009/0043718 A1 | 2/2009 | Zhang et al. |
| 2009/0150311 A1 | 6/2009 | George |
| 2009/0313193 A1 | 12/2009 | Hawkins et al. |
| 2011/0202486 A1 | 8/2011 | Fung et al. |

\* cited by examiner

US 8,898,149 B2

BIOLOGICAL DATA STRUCTURE HAVING MULTI-LATERAL, MULTI-SCALAR, AND MULTI-DIMENSIONAL RELATIONSHIPS BETWEEN MOLECULAR FEATURES AND OTHER DATA

RELATED CASES

This patent application claims the benefit of U.S. provisional patent application 61/483,248 that was filed on May 6, 2011 and is entitled "COMPUTER SYSTEM AND METHOD TO AUTOMATE KNOWLEDGE RECOVERY, INFERENCE, AND LEARNING." This patent application claims the benefit of U.S. provisional patent application 61/555,217 that was filed on Nov. 3, 2011 and is entitled "COMPUTER SYSTEM AND METHOD TO AUTOMATE KNOWLEDGE RECOVERY, INFERENCE, AND LEARNING." This patent application also claims the benefit of U.S. provisional patent application 61/596,859 that was filed on Feb. 9, 2012 and is entitled "BIOLOGICAL DATA STRUCTURE HAVING MULTI-LATERAL, MULTI-SCALAR, AND MULTI-DIMENSIONAL RELATIONSHIPS BETWEEN MOLECULAR FEATURES AND OTHER DATA." U.S. provisional patent applications 61/483,248, 61/555,217, and 61/596,859 are hereby incorporated by reference into this patent application.

TECHNICAL BACKGROUND

Breakthroughs in genomic sequencing and analysis technologies are generating vast amounts of molecular feature data for both individuals and patient groups, such as a breast cancer patient group using a specific drug. In addition, the treatments used to combat various diseases and medical conditions are also rapidly expanding. The nexus of readily-available genomics and advanced medical approaches has created the opportunity to provide personalized medicine where an individual's own genetic data can be used to develop personalized treatments based on past case histories, genetic records, and medical research.

Various approaches to data structuring have been proposed to support personalized medicine based on individual genomic data. Object-oriented data, relational databases, hyper-graphs, Bayesian networks, and hierarchical temporal memories are a few examples of such approaches. Unfortunately, these approaches do not relate knowledge and data in an effective way to efficiently and robustly support personalized medicine at the molecular level.

OVERVIEW

A computer system maintains a biological data structure having molecular feature data. The system receives data elements indicating biological molecular features and knowledge elements that represent biological concepts. The system individually associates unique identifiers with the elements. For individual elements, the system maintains an internal element set of the other unique identifiers for the other elements that are directly associated with that one individual element. For the individual elements, the system maintains an external element set of the other unique identifiers for the other elements that have that one individual element in their own internal element sets. Although not required, the computer system may process a query indicating a search scope and a molecular feature for an individual biological entity, and responsively process the molecular feature and the elements based on the search scope to induce a knowledge sub-graph for the individual biological entity.

DETAILED DESCRIPTION

Figure 1:
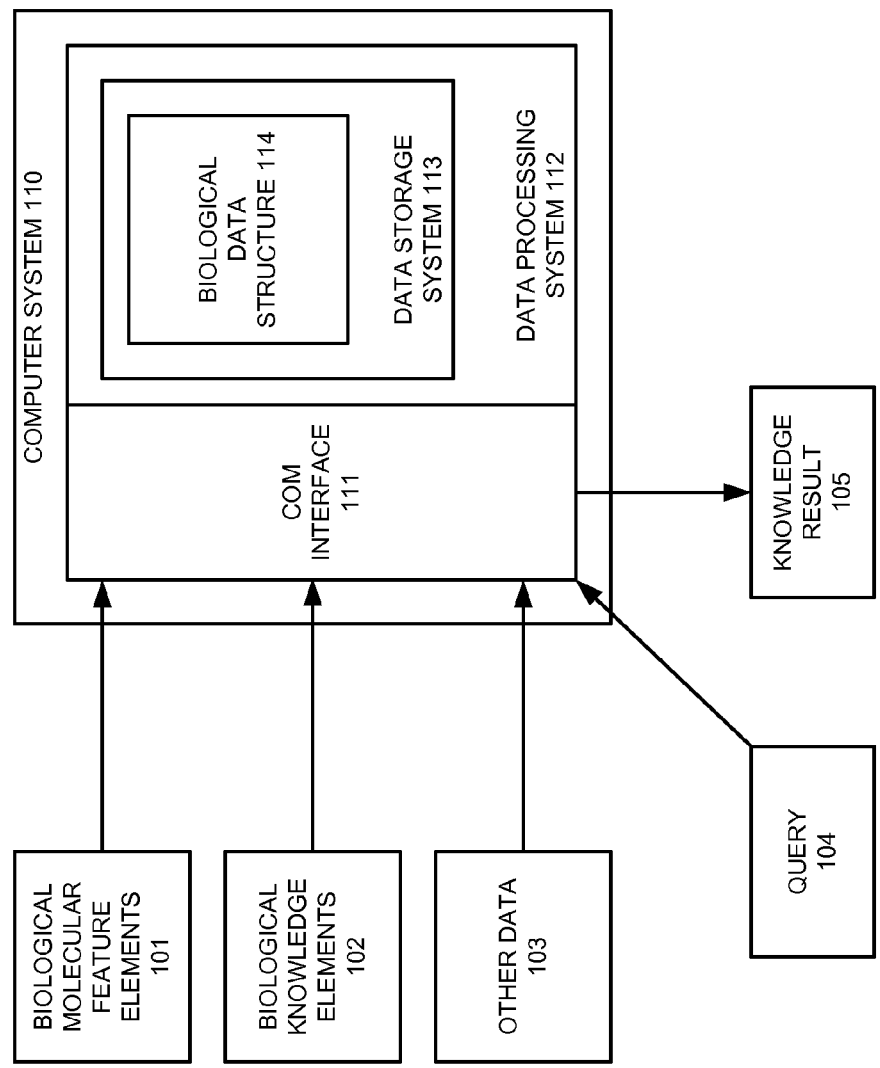
FIG. 1 illustrates a biological data system that includes a computer system to maintain a biological data structure.
Figure 2:
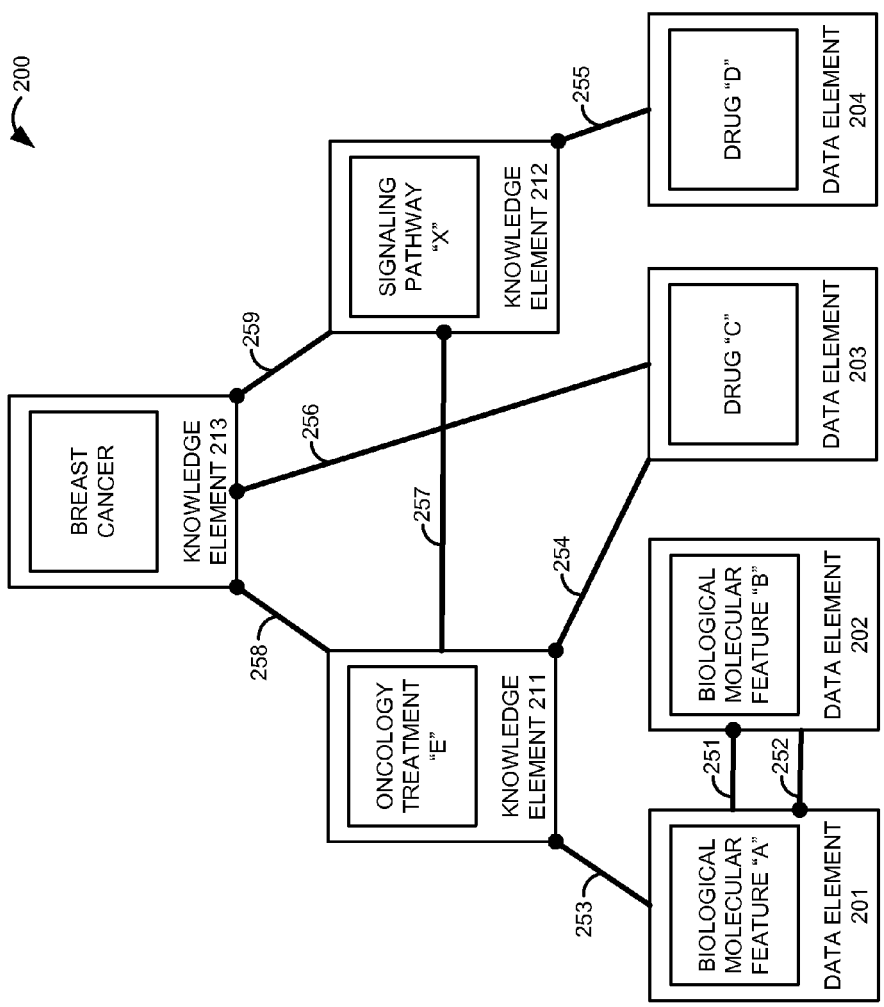
FIG. 2 shows a data structure to illustrate a data model implemented by a data processing system to maintain a biological data structure.

FIG. 1 illustrates biological data system 100 that includes computer system 110 to maintain biological data structure 114. Biological data structure 114 contains molecular feature data with a few examples being genes, gene variants, gene expression data, gene states, and the like. Computer system 110 comprises communication interface 111 and data processing system 112. Data processing system 112 includes data storage system 113 which stores biological data structure 114.

Computer system 110 is comprised of computer circuitry, memory devices, software, and communication components. Note that communication interface 111 and data systems 112-113 may be integrated together on a single platform or may be geographically distributed across multiple diverse computer and communication systems. Likewise, communication interface 111 and data systems 112-113 may individually comprise a single platform or be geographically distributed across multiple diverse computer and communication components.

In operation, communication interface 111 receives data elements 101 that indicate biological molecular features. Communication interface 111 also receives knowledge elements 102 that represent biological concepts, such as disease signatures, disease classifications, drug signatures, and drug classifications and the like. In addition, communication interface 111 receives other data 103 that may comprise other data elements, knowledge elements, attributes, data processing functions, or various other types of data and instructions. For example, the additional data elements might include drugs, drug states, diseases, and disease states. Additional knowledge elements might include oncology treatments, signaling pathways, nucleic acid repairs, and the like. Note that the distinction between data elements and knowledge elements is arbitrary within biological data system 100, and the distinction is made to help understand the full and robust capability of system 100.

Data processing system 112 individually associates a Universally Unique Identifier (UUID) with each one of data elements 101, knowledge elements 102, and also with any additional data and/or knowledge elements in other data 103. The UUID should be unique within data system 100, and in some examples, the UUID is also unique across several disparate systems. For a scenario with many diverse systems, the UUIDs generated by any given system should be statistically universally unique across all of the systems to support data mergers and queries across the systems and to support data references in systems that are not suitably referenced. In some examples, data processing system 112 also associates unique identifiers with individual attributes and/or data processing functions. Data storage system 113 stores the data elements in association with their UUIDs and other relationship data in biological data structure 114.

For individual data elements 101, data processing system 112 maintains an internal element set of the UUIDs for the other data and/or knowledge elements that are directly associated with that individual data element. For individual knowledge elements 102, data processing system 112 maintains an internal element set of the UUIDs for the other data and/or knowledge elements that are directly associated with that individual knowledge element. In a similar manner, data processing system 112 may maintain similar internal element sets of UUIDs for the data and knowledge elements in other data 103. These direct internal associations may be indicated by system personnel, table look-ups, automated rule sets, or learning algorithms. For example, Bayesian belief propagation systems, hierarchical temporal memories, and neural networks could be used to identify some of the internal relationships.

For individual data elements 101, data processing system 112 maintains an external element set of the UUIDs for the other data and knowledge elements that have that individual data element in their own internal element set. For individual knowledge elements 102, data processing system 112 maintains an external element set of the UUIDs for the other data and knowledge elements that have that individual knowledge element in their own internal element set. Likewise, data processing system 112 may maintain similar external element sets of UUIDs for the data and knowledge elements in other data 103.

Note that the terms "internal" and "external" as used herein could be replaced by other distinguishing terms as desired. For a given element, the "internal" set typically includes other elements that comprise or characterize that given element in the manner that pieces of data comprise or characterize a knowledge concept. In the various elements, the "external" sets reflect these direct "internal" relationships.

In addition to maintaining biological data structure 114, computer system 110 also processes queries to return knowledge results. Communication interface 111 receives query 104 that indicates molecular feature data for an individual biological entity, such as a gene variation for a cancer patient. Data processing system 112 processes the molecular feature data from query 104 and the data elements in data structure 114 to identify any of the data elements having corresponding biological molecular features. Pattern matching, hierarchical temporal memory, neural networks, or some other data processing technique could be used to identify the corresponding biological molecular features.

Data processing system 112 induces a knowledge subgraph for the individual biological entity based on the internal element sets and/or the external element sets of the identified data elements having the corresponding biological molecular features. In a first order search, the corresponding molecular feature elements and the first order elements listed in their external and/or internal sets are returned. In a second order search, the second order elements in the external and/or internal sets of the first order elements are also returned. At a given order, the search may be external, internal, or both depending on the search scope. In this manner, subgraphs are induced responsive to the search scope in query 104.

In biological data structure 114, the data elements may be associated with attributes and functions that have associated values and states. In these examples, data processing system 112 is configured to search data structure 114 for specific attribute types and specific function types including searching for specific attributes and functions types having specific values or states. The results of attribute/function searching could then be used to induce knowledge subgraphs as described herein.

Communication interface 111 transfers knowledge result 105 representing the induced sub-graph for the individual biological entity. For example, computer system 110 may provide a knowledge sub-graph for a cancer patient based on the patient's own specific gene variation, where the sub-graph indicates an invaluable collection of relevant data and knowledge that is specific to the patient at the molecular level.

FIGS. 2-7 show data set 200 to illustrate the data model that is implemented by data processing system 112 to maintain a biological data structure 114. Although specific types of data and knowledge elements are shown on FIGS. 2-7, these specific elements are merely exemplary, and a multitude of other data and knowledge elements would typically be used. Thus, no real-world correlations of molecular features to treatments, drugs, or other elements is intended on FIGS. 2-7.

Data set 200 includes data elements 201-204 and knowledge elements 211-213. On FIG. 2, direct relationships 251-259 are indicated by lines with dots at one end. The element on the "dot" has the internal set, and the other element on the line (no dot) is in that internal set. For example, the internal set for knowledge element 211 (oncology treatment "E") includes the UUID for data element 201 (molecular feature "A") as represented by direct relationship 253. Based on direct relationship 253, the external element set for data element 201 includes the UUID for knowledge element 211.

Note how the relationship between elements 201 and 211 has a directed aspect in that element 211 relates itself directly to element 201 in its own internal set. This relationship between elements 201 and 211 also has an undirected aspect in that element 201 relates back to element 211 through its own external set in an undirected manner. Also note how data and knowledge can be inter-related.

Knowledge element 213 is directly related to elements 203, 211, and 212 by respective relationships 256, 258, and 259. Knowledge element 211 is directly related to elements 201 and 203 by respective relationships 253 and 254. Knowledge element 212 is directly related to elements 204 and 211 by respective relationships 255 and 257. Data elements 201-202 are directly related to each other by respective relationships 251-252.

Figure 3:
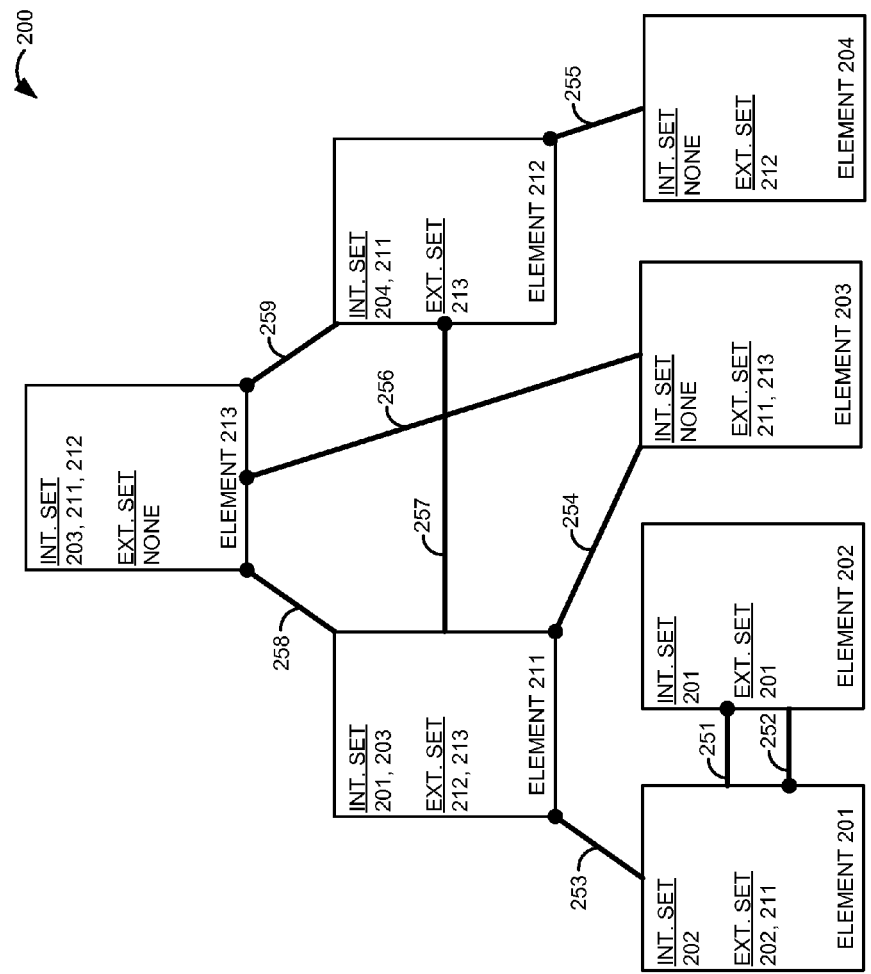
FIG. 3 further illustrates the data model implemented by the data processing system to maintain the biological data structure.

FIG. 3 shows data set 200 to further illustrate the data model for biological data structure 114. The internal element sets and the external element sets for elements 201-204 and 211-213 are now shown along with their corresponding direct relationships 251-259.

Knowledge element 213 is directly related to elements 203, 211, and 212, and as a result, element 213 indicates the UUIDs for elements 203, 211, and 212 in its internal set. Knowledge element 211 is directly related to elements 201 and 203, and as a result, element 211 indicates the UUIDs for elements 201 and 203 in its internal set. Knowledge element 212 is directly related to elements 204 and 211, and as a result, element 212 indicates the UUIDs for elements 204 and 211 in its internal set. Data elements 201-202 are directly related to each other, and as a result, elements 201-202 indicate the UUID for each other in their internal sets.

In a reciprocal fashion, element 201 is in the internal sets of elements 202 and 211, and as a result, element 201 indicates the UUIDs for elements 202 and 211 in its external set. Element 202 is in the internal set of element 201, and as a result, element 202 indicates the UUID for element 201 in its external set. Element 203 is in the internal sets of elements 211 and 213, and as a result, element 203 indicates the UUIDs for elements 211 and 213 in its external set. Element 204 is in the internal set of element 212, and as a result, element 204 indicates the UUID for element 212 in its external set. Element 211 is in the internal sets of elements 212 and 213, and as a result, element 211 indicates the UUIDs for elements 212 and 213 in its external set. Element 212 is in the internal set of element 213, and as a result, element 212 indicates the UUID for element 213 in its external set.

Figure 4:
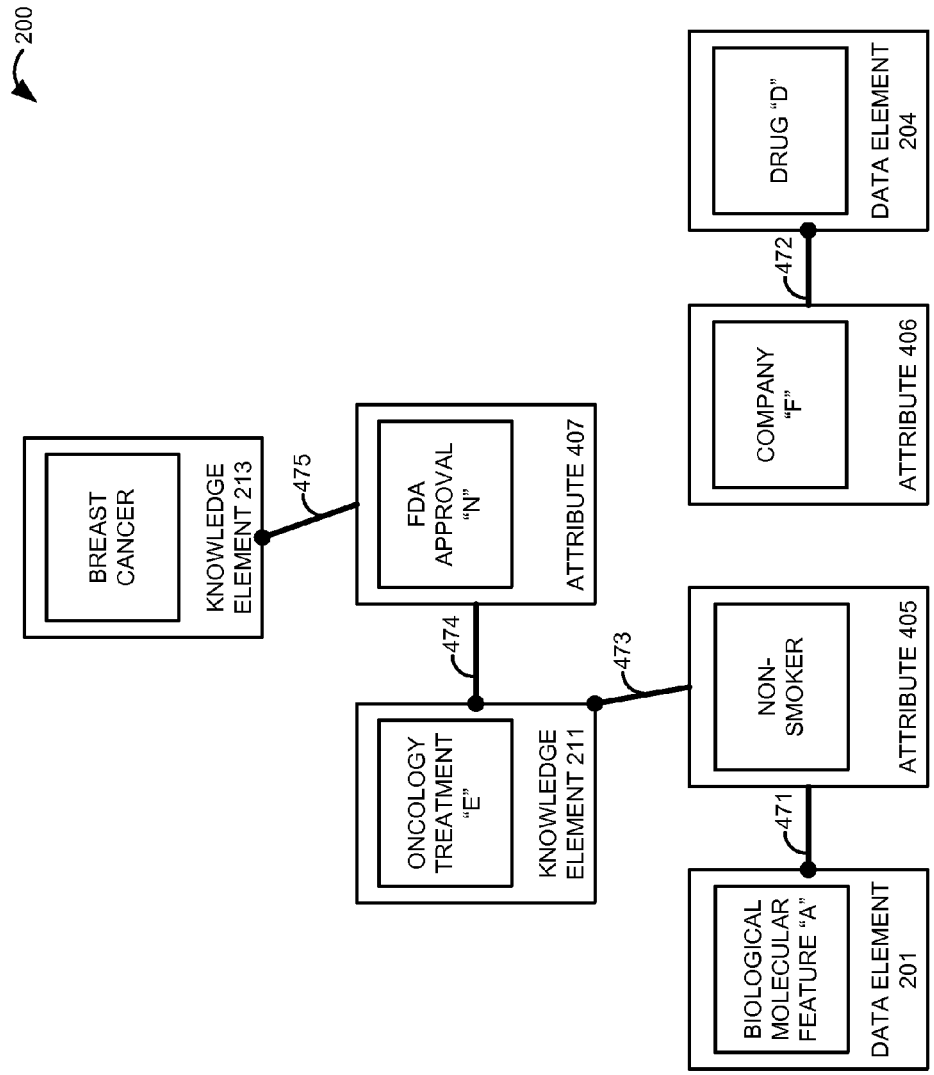
FIG. 4 illustrates attribute relationships in the data model implemented by the data processing system to maintain the biological data structure.

FIG. 4 shows data set 200 to illustrate attribute relationships in the data model implemented by data processing system 112 to maintain biological data structure 114. Data set 200 now shows elements 201, 204, 211, and 213, and attributes 405-407 have been added. Attributes 405-407 each comprise an attribute identifier (ID), a data type, and a data value. Data processing system 112 may use UUIDs to identify the attributes or use some other type of ID technique. Data attributes could comprise any data values including age, lifestyle metrics, geographic location, ethnicity, gender, project, company, status, and the like. Although specific attribute types are shown on FIG. 4, these specific attributes are merely exemplary, and a multitude of other attributes would typically be used.

On FIG. 4, attribute relationships 471-475 are also indicated by lines with dots at one end. The element on the "dot" has an attribute set, and the attribute on the line (no dot) is in that attribute set. For example, the attribute set for knowledge element 211 (oncology treatment "E") includes the attribute ID for attribute 405 (non-smoker) as represented by attribute relationship 473. Based on attribute relationship 473, the element set for attribute 405 would include the UUID for knowledge element 211. Note how various data elements and knowledge elements may share attributes. Knowledge elements 211 and 213 are both related to attribute 407 by respective attribute relationships 474-475. Data element 201 and knowledge element 211 and are both related to attribute 405 by respective attribute relationships 471 and 473. Data element 204 is related to attribute 406 by respective attribute relationship 472.

If attribute searching is supported, then data processing system 112 is configured to search biological data structure 114 (including data set 200) to identify specific attribute types or specific attribute types having specific values. For example, attribute 407 would be identified in a search for the attribute type "FDA Approval" or in a search for the attribute type "FDA Approval" having the corresponding "N" value. These searches may include combinations of elements and attributes, so a search for all oncology treatment elements with an attribute type/value of "FDA Approval N" would return knowledge element 211—"Oncology Treatment E."

Figure 5:
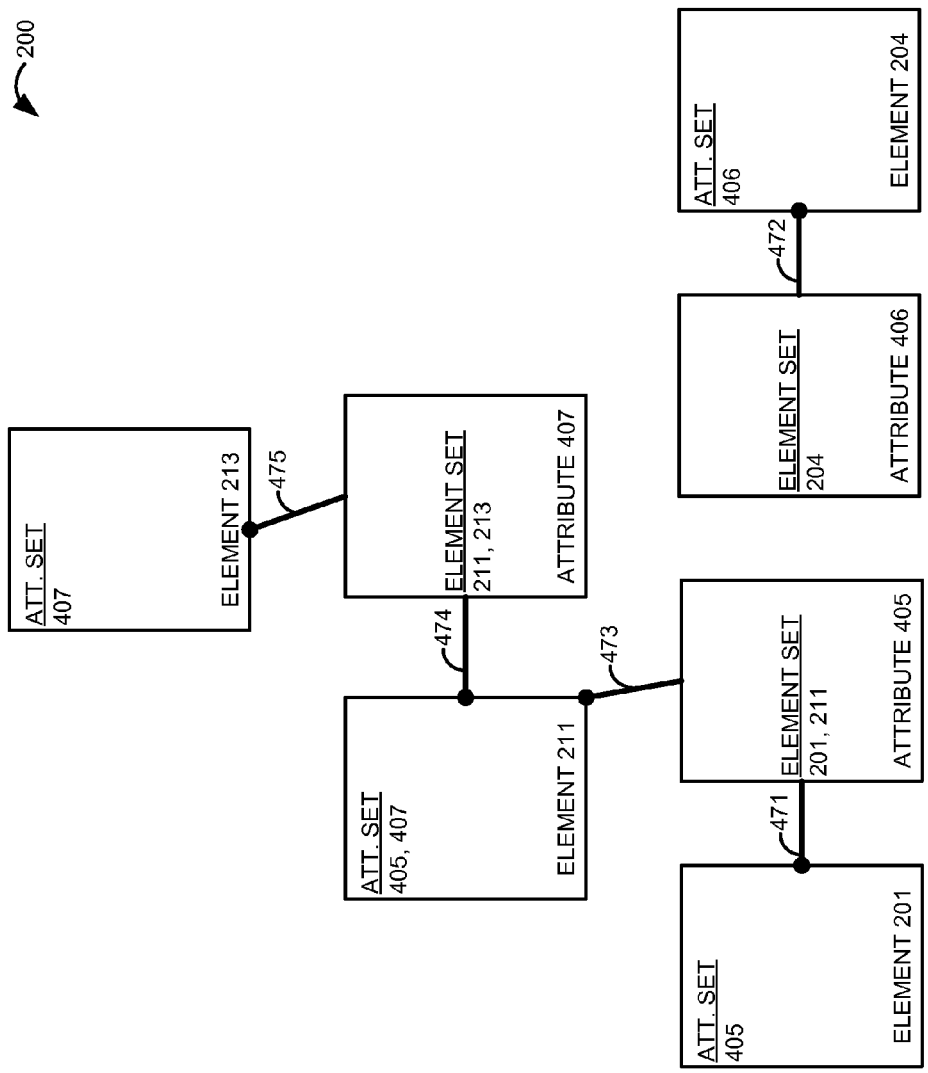
FIG. 5 further illustrates the attribute relationships.

FIG. 5 shows data set 200 to further illustrate the attribute relationships in the data model for biological data structure 114. The attribute sets for elements 201, 204, 211, and 213, and the element sets for attributes 405-407 are now shown along with their corresponding attribute relationships 471-475. Knowledge elements 211 and 213 are related to attribute 407, and as a result, elements 211 and 213 each indicate the ID for attribute 407 in their attribute set. Data element 201 and knowledge element 211 are related to attribute 405, and as a result, elements 201 and 211 each indicate the ID for attribute 405 in their attribute set. Data element 204 is related to attribute 406, and as a result, element 204 indicates the ID for attribute 406 in its attribute set.

In a reciprocal fashion, attribute 405 is in the attribute sets of elements 201 and 211, and as a result, attribute 405 indicates the UUIDs for elements 201 and 211 in its element set. Attribute 406 is in the attribute set of element 204, and as a result, attribute 406 indicates the UUID for element 204 in its element set. Attribute 407 is in the attribute sets of elements 211 and 213, and as a result, attribute 407 indicates the UUIDs for elements 211 and 213 in its element set.

Figure 6:
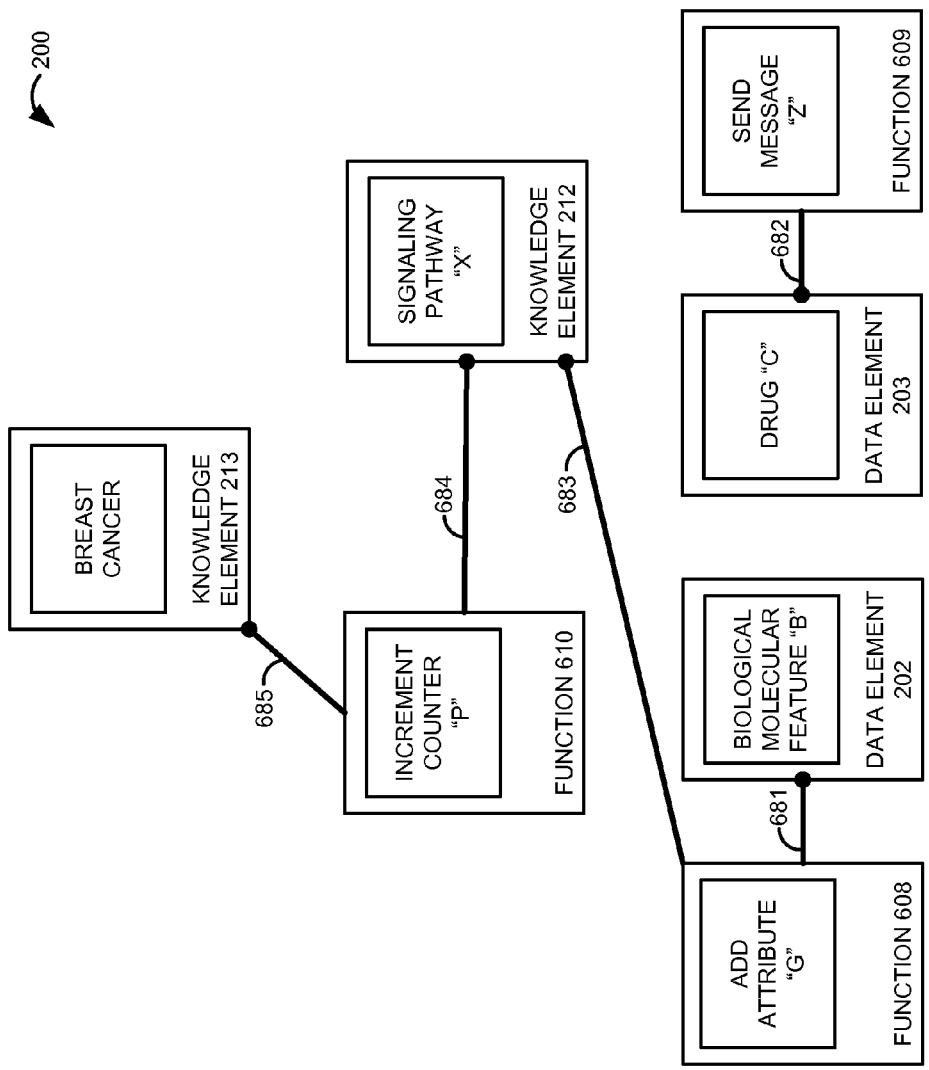
FIG. 6 illustrates function relationships in the data model implemented by the data processing system to maintain the biological data structure.

FIG. 6 shows data set 200 to illustrate function relationships in the data model implemented by data processing system 112 to maintain biological data structure 114. Data structure 200 now shows elements 202, 203, 212, and 213, and functions 608-610 have been added. Functions 608-610 each comprise a function identifier (ID), a function type, and function logic. Data processing system 112 may use UUIDs to identify the functions or use some other type of ID technique. Data functions could be event handlers, message triggers, or some other data processing task. Although specific function types are shown on FIG. 6, these specific functions are merely exemplary, and a multitude of other functions would typically be used.

Data processing system 112 executes the data processing functions directly associated with a data or knowledge element when it handles that element in data structure 114. For example, the knowledge element for a specific form of carcinoma may have a notice function to email a key research scientist whenever the carcinoma knowledge element is handled in a specific context. In other cases, data processing system 112 may invoke functions based on external events and conditions. For example, a given data element may have a delete function for Dec. 31, 2018, and when data processing system 112 eventually receives the event that today is Dec. 31, 2018, it searches for Dec. 31, 2108 event functions and responsively deletes the given data element from the system.

If function searching is supported, then data processing system 112 is configured to search biological data structure 114 (including data set 200) to identify specific function types or specific function types having specific values or states. For example, function 609 would be identified in a search for the function type "Send Message" or in a search for the function type "Send Message" having the corresponding "Z" value. These searches may include combinations of elements, attributes, and functions, so a search for all drug data elements with a function type/value of "Send Message Z" would return data element 203—"Drug C."

On FIG. 6, function relationships 681-685 are also indicated by lines with dots at one end. The element on the "dot" has a function set, and the function on the line (no dot) is in that function set. For example, the function set for knowledge element 212 (signaling pathway "X") includes the function ID for function 610 (increment counter "P") as represented by function relationship 684. Based on function relationship 684, the element set for function 610 would include the UUID for knowledge element 212. Note how various data elements and knowledge elements may share functions. Knowledge element 212 and 213 are both related to function 610 by respective function relationships 684-685. Data element 202 and knowledge element 212 and are both related to function 608 by respective function relationships 681 and 683. Data element 203 is related to function 609 by respective function relationship 682.

Figure 7:
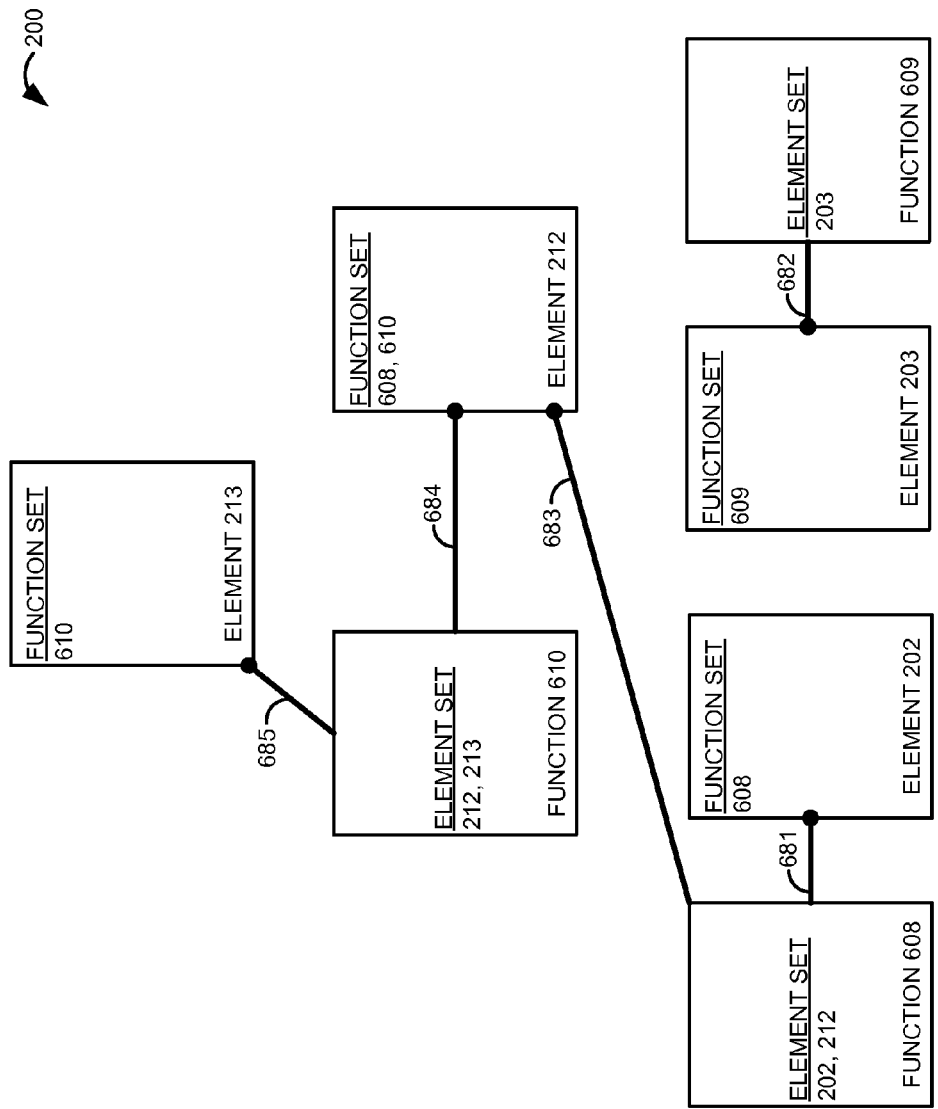
FIG. 7 further illustrates the function relationships.

FIG. 7 shows data set 200 to further illustrate the function relationships in the data model for biological data structure 114. The function sets for elements 202, 203, 212, and 213, and the element sets for functions 608-610 are now shown along with their corresponding function relationships 681-685. Knowledge elements 212 and 213 are related to function 610, and as a result, elements 212 and 213 each indicate the function ID for function 610 in their function set. Data element 202 and knowledge elements 212 are related to function 608, and as a result, elements 202 and 212 each indicate the ID for function 608 in their function set. Data element 203 is related to function 609, and as a result, element 203 indicates the ID for function 609 in its function set.

In a reciprocal fashion, function 608 is in the function set of elements 202 and 212, and as a result, function 608 indicates the UUIDs for elements 202 and 212 in its element set. Function 609 is in the function set of element 203, and as a result, function 609 indicates the UUID for element 203 in its element set. Function 610 is in the function sets of elements 212 and 213, and as a result, function 610 indicates the UUIDs for elements 212 and 213 in its element set.

FIGS. 8-11 illustrate various search techniques implemented by data processing system 112 to retrieve knowledge from biological data structure 114. Note that these search technique are examples, and data processing system 112 may use other search techniques. It should be appreciated that these techniques could be combined and modified in various ways to provide a myriad of different search opportunities. For clarity, the amount and complexity of the searches, data elements, and knowledge elements has been restricted on FIGS. 8-11.

Figure 8:
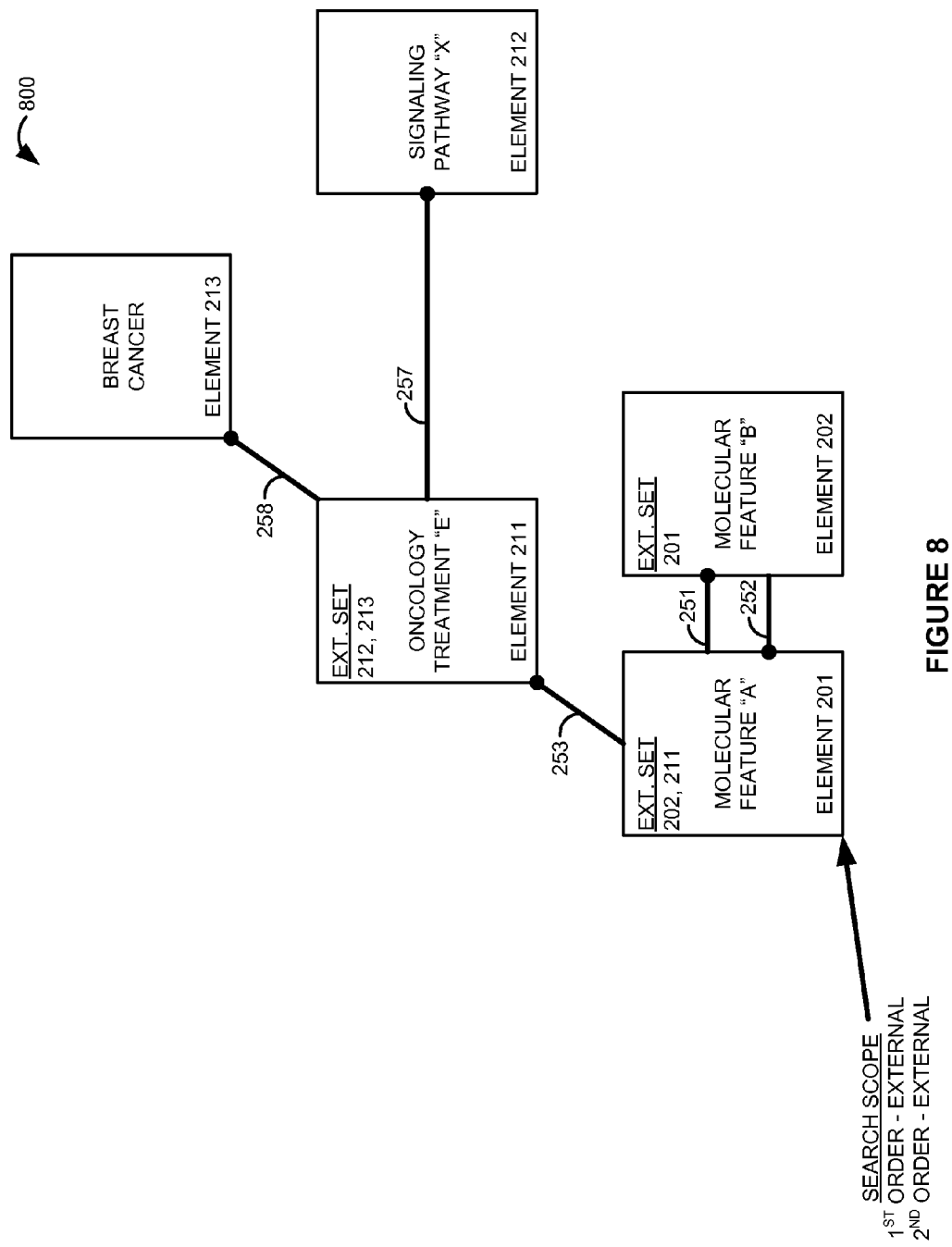
FIG. 8 illustrates a knowledge sub-graph induced by an external/external second order search through the biological data structure.

FIG. 8 illustrates knowledge sub-graph 800 induced by a search through biological data structure 114, where the search scope is first order external and second order external. Prior to inducing sub-graph 800, data processing system 112 receives query 104 indicating a biological molecular feature for an individual cancer patient. Query 104 also indicates the search scope: first order external and second order external. Responsive to query 104, data processing system 112 identifies data element 201 (molecular feature "A") through molecular level pattern matching, attribute/function searching, or some other molecular feature search technique.

To induce sub-graph 800 responsive to the search scope, data processing system 112 initiates a first order external search by processing the external set of data element 201 to identify elements 202 and 211 and their corresponding first order relationships 251 and 253. For the second order external search, data processing system 112 processes the external sets of data element 202 and 211 from the first order search to identify elements 201 and 212-213 and their corresponding second order relationships 252 and 257-258. Data processing system 112 transfers knowledge result 105 indicating sub-graph 800 in response to query 104. Note that the search paths from element 201 to elements 212-213 are readily identifiable from knowledge result 105.

Figure 9:
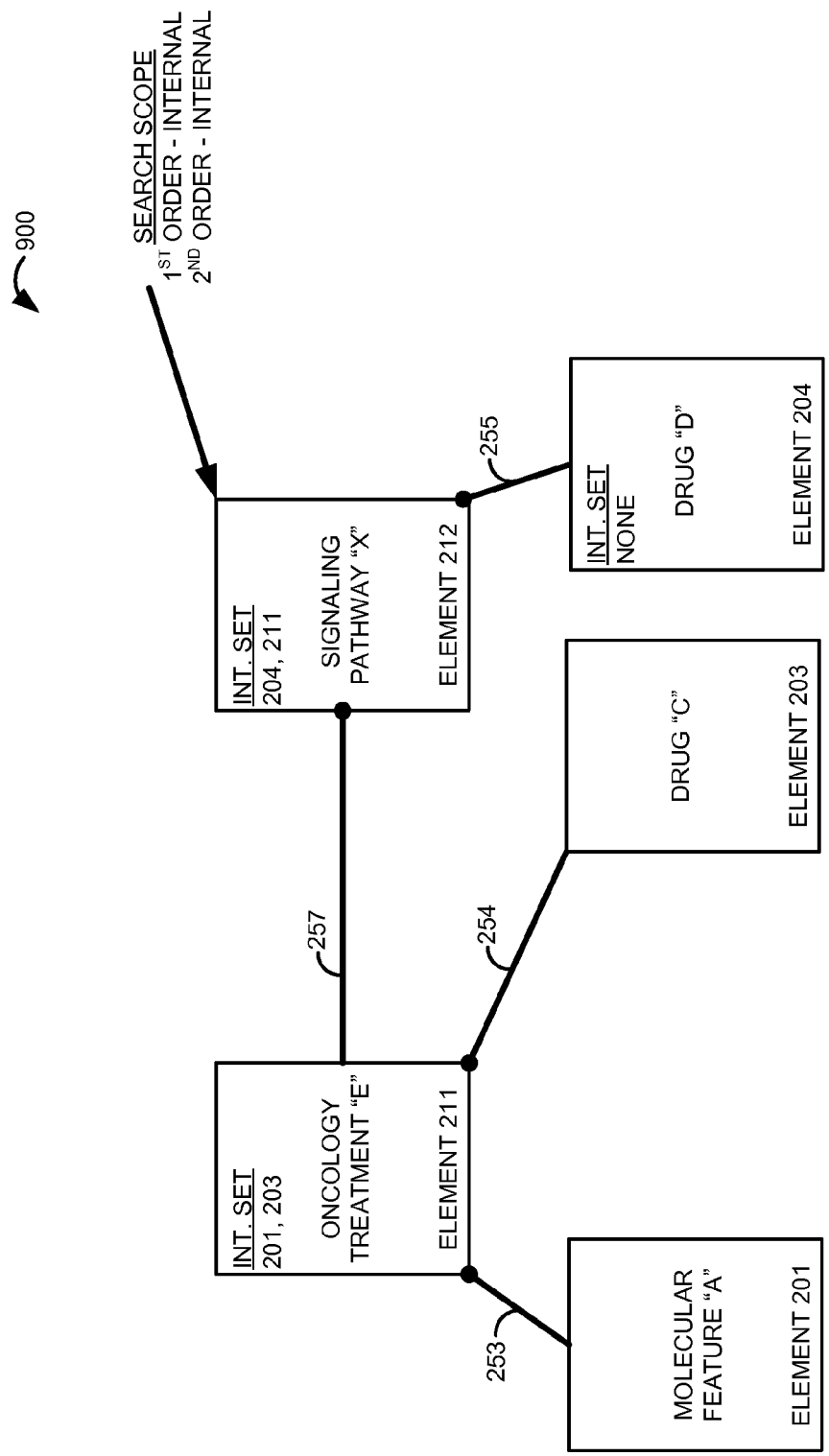
FIG. 9 illustrates a knowledge sub-graph induced by an internal/internal second order search through the biological data structure.

FIG. 9 illustrates knowledge sub-graph 900 induced by a search through biological data structure 114, where the search scope is first order internal and second order internal. Prior to inducing sub-graph 900, data processing system 112 receives query 104 indicating signaling pathway "X" based on a medical diagnosis for an individual cancer patient. Query 104 also indicates the search scope: first order internal and second order internal. Responsive to query 104, data processing system 112 identifies data element 212 (signaling pathway "X") from a semantic analysis of query 104, attribute/function searching, or some other query analysis technique.

To induce sub-graph 900 responsive to the search scope, data processing system 112 initiates a first order internal search by processing the internal set of element 212 to identify elements 204 and 211 and their corresponding first order relationships 255 and 257. For the second order internal search, data processing system 112 processes the internal sets of data elements 204 and 211 from the first order search to identify elements 201 and 203 and their corresponding second order relationships 253-254. Data processing system 112 transfers knowledge result 105 indicating sub-graph 900 in response to query 104. Note that the search paths from element 212 to elements 201-203 are readily identifiable from knowledge result 105.

Figure 10:
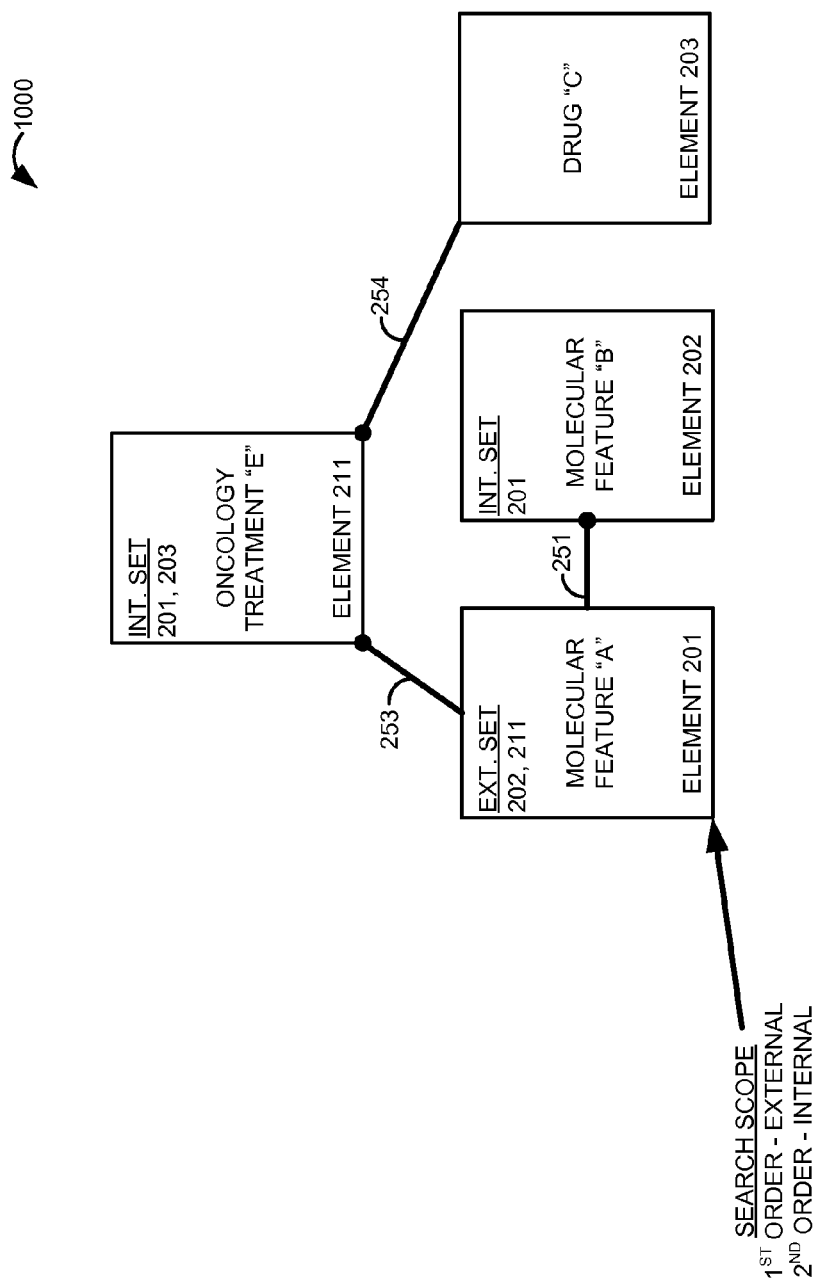
FIG. 10 illustrates a knowledge sub-graph induced by an external/internal second order search through the biological data structure.

FIG. 10 illustrates knowledge sub-graph 1000 induced by a search through biological data structure 114, where the search scope is first order external and second order internal. Prior to inducing sub-graph 1000, data processing system 112 receives query 104 indicating the biological molecular features of an individual cancer patient. Query 104 also indicates the search scope: first order external and second order internal. Responsive to query 104, data processing system 112 identifies data element 201 (molecular feature "A") through molecular level pattern matching, attribute/function searching, or some other molecular feature search technique.

To induce sub-graph 1000 responsive to the search scope, data processing system 112 initiates a first order external search by processing the external set of data element 201 to identify elements 202 and 211 and their corresponding first order relationships 251 and 253. For the second order internal search, data processing system 112 processes the internal sets of data element 202 and 211 from the first order search to identify elements 201 and 203 and their corresponding second order relationships 251 and 254. Data processing system 112 transfers knowledge result 105 indicating sub-graph 1000 in response to query 104. Note that the search paths from element 201 to elements 201 and 203 are readily identifiable from knowledge result 105.

Figure 11:
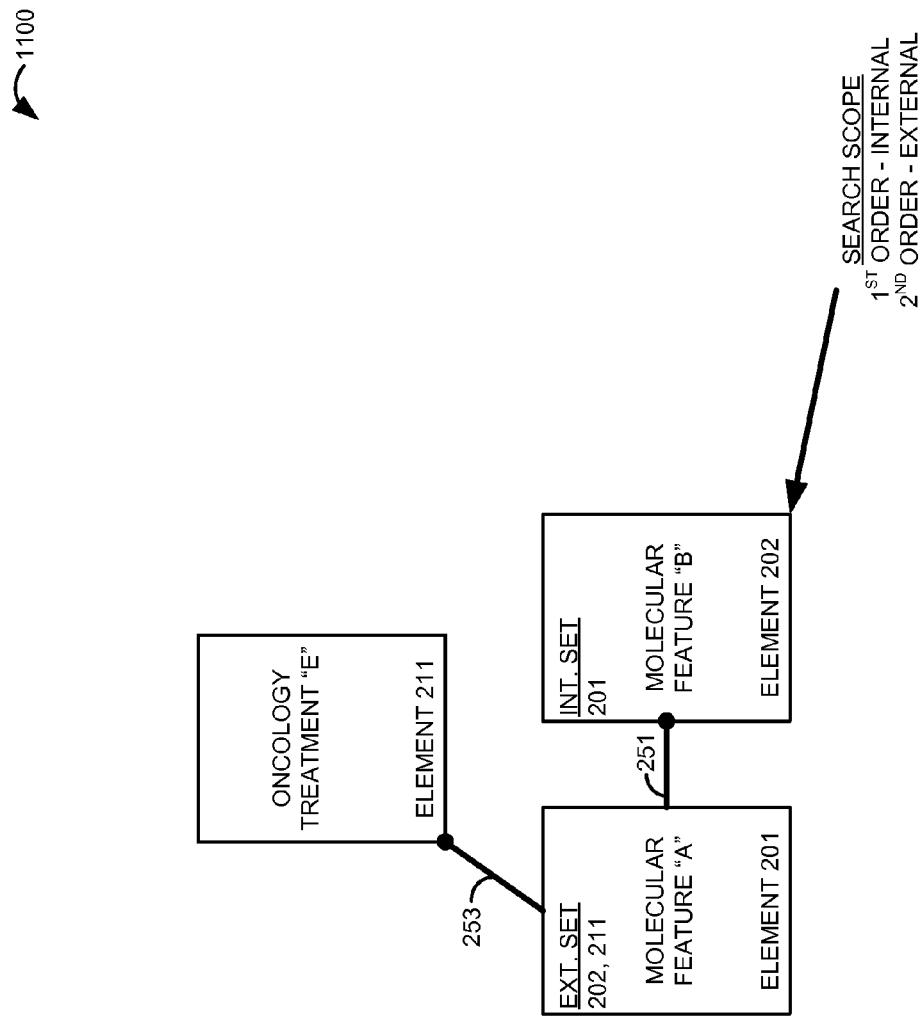
FIG. 11 illustrates a knowledge sub-graph induced by an internal/external second order search through the biological data structure.

FIG. 11 illustrates knowledge sub-graph 1100 induced by a search through biological data structure 114, where the search scope is first order internal and second order external. Prior to inducing sub-graph 1100, data processing system 112 receives query 104 indicating the biological molecular features of an individual cancer patient. Query 104 also indicates the search scope: first order internal and second order external. Responsive to query 104, data processing system 112 identifies data element 202 (molecular feature "B") through molecular level pattern matching, attribute/function searching, or some other molecular feature search technique.

To induce sub-graph 1100 responsive to the search scope, data processing system 112 initiates a first order internal search by processing the internal set of data element 202 to identify element 201 and the corresponding first order relationship 251. For the second order external search, data processing system 112 processes the external set of data element 201 from the first order search to identify elements 202 and 211 and their corresponding second order relationships 251 and 253. Data processing system 112 transfers knowledge result 105 indicating sub-graph 1100 in response to query 104. Note that the search paths from element 202 to elements 202 and 211 are readily identifiable from knowledge result 105.

Note that a full (internal and external) search could be performed at any given order by combining internal and external search results for that order. Also note that different types of searches may be specified at the different orders—like a full first order full search combined with an internal second order search. Note that the search order could be increased or decreased as well, and a first order search, third order search, tenth order search, or some other order search could be performed used using the principles described herein. In addition, a search may not be limited to a given order and may be allowed to recursively traverse the element sets in an indefinite manner. It may be desirable to provide a user interface that allows the user to toggle between various search inputs, search scopes, and sub-graphs and to uncover relevant knowledge.

Also note that various rules could be applied to the data model described above. For example, a rule could be imposed that requires all elements to have an attribute with a value of "directed" or "undirected." For elements with the directed attribute, another rule might stipulate that their internal element sets are ordered lists. In another example, a rule and corresponding attribute value may force an element to have an empty internal set, and thus, to behave like a node in a hypergraph. In yet another example, a rule and corresponding attribute values of "node" or "edge" could be used to prevent "node" elements from having other attributes while allowing "edge" elements to have attributes. For a directed hypergraph, a "mode" attribute could be used with various values and rules that force the desired directed hypergraph characteristics. For a relational database, the database fields could be attributes, and the rules would enforce the desired relational database constraints.

In some examples, a control language may be used to search and maintain the data structure. The language could have persistent commands to create, modify, or remove elements, attributes, and functions. The language could have commands to induce subgraphs, such as recover, context, and expand commands to respectively induce internal and external, external-only, or internal-only subgraphs. The language could have commands to control the orders of the search and a format that allows different graph-induction approaches at each order of the search.

Figure 12:
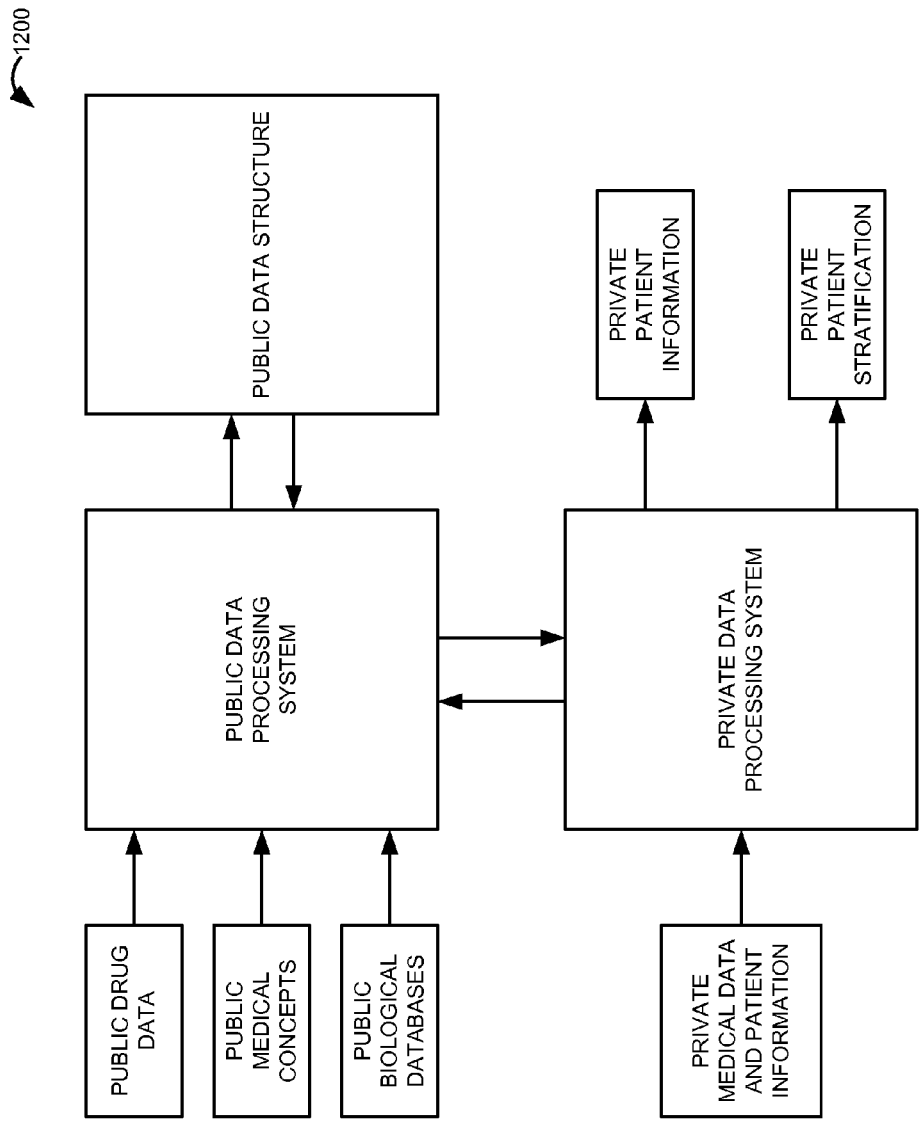
FIG. 12 illustrates a bio-intelligence system including a public data structure that uses the data model.

FIG. 12 illustrates bio-intelligence data system 1200 including a public data structure that is configured and operates like data structure 114. A public data processing system receives public drug data, medical concepts, and biological data (including public molecular feature data). The public data processing system formats and relates this public data in the public data structure as described above.

A private data processing system receives private medical and patient data. The private data processing system submits a query through the public data processing system to the public data structure. Although based on private patient data, the query is configured to maintain patient privacy. For example, the private patient name may be replaced by an anonymous code in the query.

The public data processing system induces a knowledge subgraph from the public data structure responsive to the query. The public data processing system transfers the knowledge subgraph to the private data processing system. The private data processing system interface then integrates the private patient data with the knowledge subgraph to provide a rich set of public and private patient data to facilitate a more personalized medical approach. In a similar manner, the private data processing system may integrate private patient data with knowledge subgraphs to stratify patients for various private drug trials.

Figure 13:
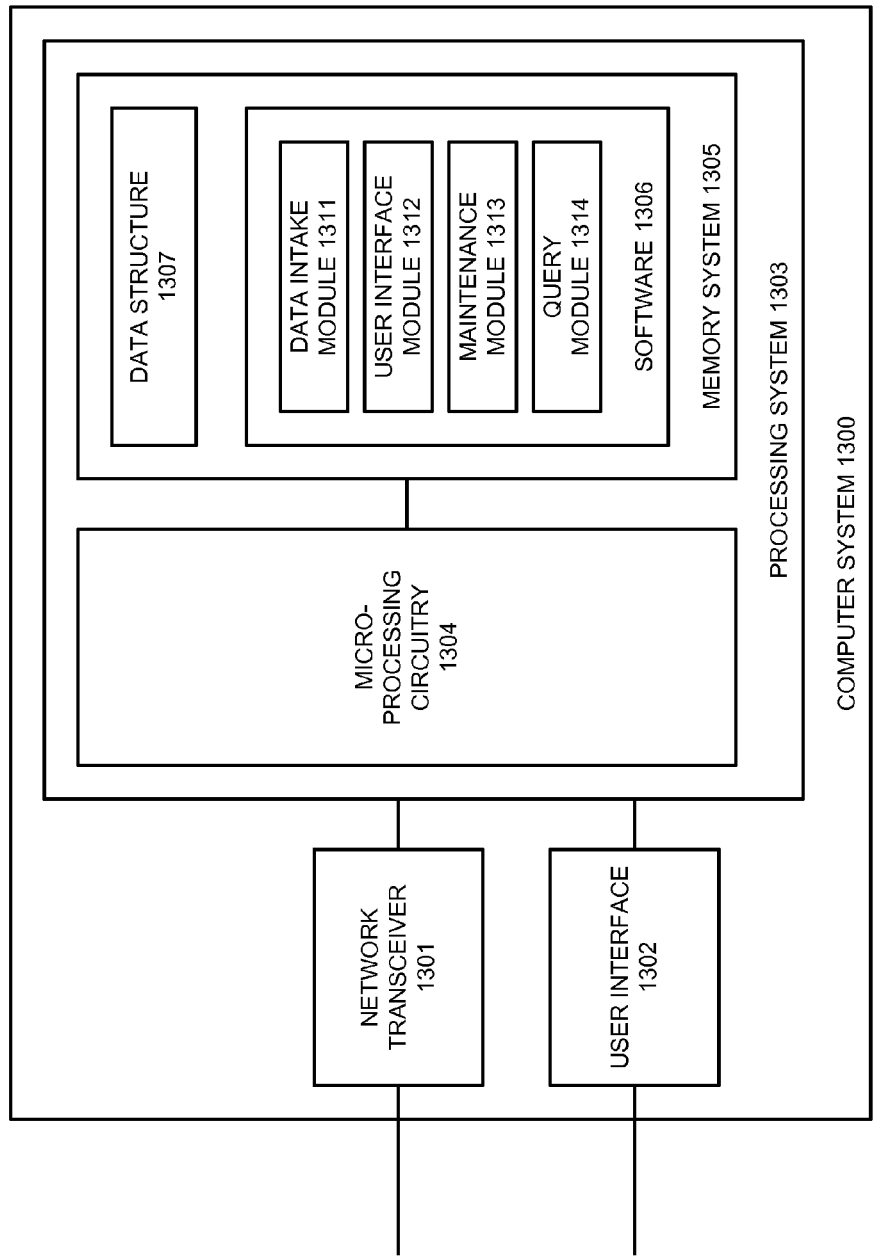
FIG. 13 illustrates a computer system to implement the data model to maintain the biological data structure.

FIG. 13 illustrates computer system 1300 to implement the data model to maintain biological data structure 1307 as described above. Computer system 1300 provides an example of computer system 110, although computer system 110 could use alternative configurations. Computer system 1300 comprises network transceiver 1301, user interface 1302, and processing system 1303. Processing system 1303 is linked to transceiver 1301 and user interface 1302. Processing system 1303 includes micro-processing circuitry 1304 and memory system 1305 that stores software 1306 and data structure 1307. Software 1306 includes software modules 1311-1314. Computer system 1300 may include other well-known components such as power supplies and enclosures that are not shown for clarity.

Network transceiver 1301 comprises communication circuitry and software for network communications. Network transceiver 1301 may use various protocols, such as Ethernet, Internet Protocol, and the like. Network transceiver 1301 receives data elements, knowledge elements, user instructions, and queries. Network transceiver 1301 transfers knowledge subgraphs. User interface 1302 comprises displays, input keys, mouse devices, touch pads, and the like.

Micro-processing circuitry 1304 comprises integrated circuitry that retrieves and executes software 1306 from memory system 1305 to maintain data structure 1307. Memory system 1305 comprises one or more non-transitory storage media, such as disk drives, flash drives, data storage circuitry, or some other memory apparatus. Processing circuitry 1304 is typically mounted on circuit boards that may also hold components of memory system 1305, transceiver 1301, and user interface 1302. Software 1306 comprises computer programs, firmware, or some other form of machine-readable processing instructions. Software 1306 may include operating systems, utilities, drivers, network interfaces, applications, or some other type of software.

When executed by micro-processing circuitry 1304, data intake module 1311 directs processing system 1303 to receive and format data and knowledge elements for data structure 1307. When executed by micro-processing circuitry 1304, user interface module 1312 directs processing system 1303 to process user instructions that specify elements, attributes, functions, and element relationships for data structure 1307. When executed by micro-processing circuitry 1304, maintenance module 1313 directs processing system 1303 to maintain element, attribute, and function sets as described above. When executed by micro-processing circuitry 1304, query module 1314 directs processing system 1303 to induce subgraphs based on the information and search scope in the queries and the user instructions. Although not shown on FIG. 13, software 1306 may also include pattern matching logic to match biological molecular features or other analytical software to indicate element relationships.

The above examples deal with biological data and knowledge. Computer systems 110 and 1300 could also be operated to maintain and search with different types of data utilizing the data model described herein. Thus, the above teachings could be deployed in other technical areas, such as genealogy, demographics, or some other type of data structure or search engine.

The above description and associated figures teach the best mode of the invention. The following claims specify the scope of the invention. Note that some aspects of the best mode may not fall within the scope of the invention as specified by the claims. Those skilled in the art will appreciate that the features described above can be combined in various ways to form multiple variations of the invention. As a result, the invention is not limited to the specific embodiments described above, but only by the following claims and their equivalents.

What is claimed is:

1. A method of operating computer system to maintain a biological data structure having molecular feature data, the method comprising: receiving data elements indicating biological molecular features and receiving knowledge elements that represent biological concepts; individually associating unique identifiers with the data elements; for individual ones of the data elements, maintaining an internal data element set of the other unique identifiers for the other data elements and knowledge elements that are directly associated with that one individual data element; and for the individual ones of the data elements, maintaining an external data element set of the other unique identifiers for the other data elements that have that one individual data element in their own internal data element sets, said method further comprising: receiving a data query indicating the molecular feature data for an individual biological entity and a search scope indicator; processing the molecular feature data and the data elements to identify ones of the data elements having corresponding biological molecular features; if the search scope indicator comprises an internal and external scope, then generating a knowledge sub-graph for the individual biological entity based on both the internal data element sets and the external data element sets of the identified data elements having the corresponding biological molecular features; if the search scope indicator comprises an internal scope, then generating the knowledge sub-graph for the individual biological entity based on the internal data element sets but not the external data element sets of the identified data elements having the corresponding biological molecular features; and if the search scope indicator comprises an external scope, then generating the knowledge sub-graph for the individual biological entity based on the external data element sets but not the internal data element sets of the identified data elements having the corresponding biological molecular features.

2. A computer apparatus to operate a computer system to maintain a biological data structure, the computer apparatus comprising: at least one non-transitory computer-readable media having computer-useable instructions embodied thereon; the computer-useable instructions configured to direct the computer system, when executed by the computer system, to receive data elements indicating biological molecular features and receive knowledge elements that represent biological concepts, to individually associate unique identifiers with the data elements, to maintain, for individual ones of the data elements, an internal data element set of the other unique identifiers for the other data elements and knowledge elements that are directly associated with that one individual data element, and to maintain, for the individual ones of the data elements, an external data element set of the other unique identifiers for the other data elements that have that one individual data element in their own internal data element sets, wherein the computer-useable instructions are configured to direct the computer system to: receive a data query indicating the molecular feature data for an individual biological entity and a search scope indicator; process the molecular feature data and the data elements to identify ones of the data elements having corresponding biological molecular features; if the search scope indicator comprises an internal and external scope, then generate a knowledge sub-graph for the individual biological entity based on both the internal data element sets and the external data element sets of the identified data elements having the corresponding biological molecular features; if the search scope indicator comprises an external scope, then generating the knowledge sub-graph for the individual biological entity based on the external data element sets but not the internal data element sets of the identified data elements having the corresponding biological molecular features; and if the search scope indicator comprises an internal scope, then generating the knowledge sub-graph for the individual biological entity based on the internal data element sets but not the external data element sets of the identified data elements having the corresponding biological molecular features.

* * * * *